United States Patent
Butler et al.

(10) Patent No.: US 10,780,231 B2
(45) Date of Patent: Sep. 22, 2020

(54) DRIVE MECHANISM FOR A DRUG DELIVERY DEVICE AND DRUG DELIVERY DEVICE

(71) Applicant: SANOFI-AVENTIS DEUTSCHLAND GMBH, Frankfurt am Main (DE)

(72) Inventors: Stephen David Butler, South Staffordshire (GB); Mark Philip Horlock, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 627 days.

(21) Appl. No.: 14/423,736

(22) PCT Filed: Sep. 9, 2013

(86) PCT No.: PCT/EP2013/068549
§ 371 (c)(1),
(2) Date: Feb. 25, 2015

(87) PCT Pub. No.: WO2014/040929
PCT Pub. Date: Mar. 20, 2014

(65) Prior Publication Data
US 2015/0238699 A1    Aug. 27, 2015

(30) Foreign Application Priority Data

Sep. 11, 2012 (EP) .................................. 12183800

(51) Int. Cl.
*A61M 5/315* (2006.01)
(52) U.S. Cl.
CPC .......... *A61M 5/3158* (2013.01); *A61M 5/3157* (2013.01); *A61M 5/31555* (2013.01); *A61M 2205/581* (2013.01); *A61M 2205/582* (2013.01)

(58) Field of Classification Search
CPC .......... A61M 5/00; A61M 5/178; A61M 5/20; A61M 5/24; A61M 5/28; A61M 5/30;
(Continued)

(56) References Cited

U.S. PATENT DOCUMENTS

| 533,575 A | 2/1895 | Wilkens |
|---|---|---|
| 4,865,591 A | 9/1989 | Sams |

(Continued)

FOREIGN PATENT DOCUMENTS

| CA | 2138528 C | 12/1998 |
|---|---|---|
| CA | 2359375 A1 | 7/2000 |

(Continued)

OTHER PUBLICATIONS

International Search Report for Int. App. No. PCT/EP2013/068549, completed Sep. 20, 2013.
(Continued)

*Primary Examiner* — Scott J Medway
(74) *Attorney, Agent, or Firm* — Fish & Richardson P.C.

(57) ABSTRACT

The present invention concerns a drive mechanism for a drug delivery device comprising a housing having a longitudinal axis, a first feedback element which is movable along the longitudinal axis relative to the housing and a second feedback element, wherein the first feedback element and the second feedback element are adapted to interact with each other thereby providing at least one of tactile and audible feedback during at least one of a dose setting and dose dispensing operation of the drive mechanism. Moreover a drug delivery device incorporating such a drive mechanism is disclosed.

13 Claims, 5 Drawing Sheets

(58) Field of Classification Search
CPC .......... A61M 5/31; A61M 5/315; A61M 5/32; A61M 2005/3247; A61M 5/3245; A61M 5/3271; A61M 5/3158; A61M 2205/581; A61M 2205/582; A61M 5/31555; A61M 5/3157

See application file for complete search history.

(56) References Cited

U.S. PATENT DOCUMENTS

| | | | |
|---|---|---|---|
| 5,092,842 | A | 3/1992 | Bechtold et al. |
| 5,226,895 | A | 6/1993 | Harris |
| 5,226,896 | A | 7/1993 | Harris |
| 5,279,586 | A | 1/1994 | Balkwill |
| 5,304,152 | A | 4/1994 | Sams |
| 5,320,609 | A | 6/1994 | Haber et al. |
| 5,378,233 | A | 1/1995 | Haber et al. |
| 5,383,865 | A | 1/1995 | Michel |
| 5,391,157 | A | 2/1995 | Harris et al. |
| 5,480,387 | A | 1/1996 | Gabriel et al. |
| 5,505,704 | A | 4/1996 | Pawelka et al. |
| 5,582,598 | A * | 12/1996 | Chanoch ............ A61M 5/31551 222/309 |
| 5,626,566 | A | 5/1997 | Petersen et al. |
| 5,674,204 | A | 10/1997 | Chanoch |
| 5,688,251 | A | 11/1997 | Chanoch |
| 5,807,346 | A | 9/1998 | Frezza |
| 5,820,602 | A | 10/1998 | Kovelman et al. |
| 5,851,079 | A | 12/1998 | Horstman et al. |
| 5,921,966 | A | 7/1999 | Bendek et al. |
| 5,957,896 | A | 9/1999 | Bendek et al. |
| 5,961,495 | A | 10/1999 | Walters et al. |
| 6,004,297 | A | 12/1999 | Steenfeldt-Jensen et al. |
| 6,193,698 | B1 | 2/2001 | Kirchhofer et al. |
| 6,221,046 | B1 | 4/2001 | Burroughs et al. |
| 6,235,004 | B1 | 5/2001 | Steenfeldt-Jensen et al. |
| 6,248,095 | B1 | 6/2001 | Giambattista et al. |
| 6,562,006 | B1 | 5/2003 | Hjertman et al. |
| 6,613,023 | B2 | 9/2003 | Kirchhofer et al. |
| 6,699,224 | B2 | 3/2004 | Kirchhofer et al. |
| 6,899,698 | B2 | 5/2005 | Sams |
| 6,932,794 | B2 | 8/2005 | Giambattista et al. |
| 6,936,032 | B1 | 8/2005 | Bush, Jr. et al. |
| 6,945,961 | B2 | 9/2005 | Miller et al. |
| 7,169,132 | B2 | 1/2007 | Bendek et al. |
| 7,241,278 | B2 | 7/2007 | Moller |
| 7,678,084 | B2 | 3/2010 | Judson et al. |
| 7,850,662 | B2 | 12/2010 | Veasey et al. |
| 8,187,233 | B2 | 5/2012 | Harms et al. |
| 8,366,680 | B2 * | 2/2013 | Raab ................ A61M 5/31555 604/207 |
| 8,663,201 | B2 * | 3/2014 | Hill .................. A61M 5/14244 600/316 |
| 8,968,256 | B2 * | 3/2015 | Raab ................ A61M 5/31543 604/211 |
| 9,283,325 | B2 * | 3/2016 | Karlsson .............. A61M 5/20 |
| 9,345,841 | B2 * | 5/2016 | Plumptre ............. A61M 5/24 |
| 9,421,334 | B2 * | 8/2016 | Quinn ............... A61M 5/31541 |
| 9,457,154 | B2 * | 10/2016 | Moller ................ A61M 5/20 |
| 2002/0052578 | A1 | 5/2002 | Moller |
| 2002/0120235 | A1 | 8/2002 | Enggaard |
| 2003/0050609 | A1 | 3/2003 | Sams |
| 2003/0114836 | A1 * | 6/2003 | Estes ................ A61M 5/14244 604/890.1 |
| 2003/0120209 | A1 * | 6/2003 | Jensen ................ A61M 5/326 604/110 |
| 2004/0059299 | A1 | 3/2004 | Moller |
| 2004/0097883 | A1 | 5/2004 | Roe |
| 2004/0210199 | A1 | 10/2004 | Atterbury et al. |
| 2004/0267207 | A1 | 12/2004 | Veasey et al. |
| 2005/0020979 | A1 * | 1/2005 | Westbye ............ A61M 5/2033 604/151 |
| 2005/0113765 | A1 | 5/2005 | Veasey et al. |
| 2006/0153693 | A1 | 7/2006 | Fiechter et al. |
| 2007/0016143 | A1 | 1/2007 | Miller et al. |
| 2007/0123829 | A1 * | 5/2007 | Atterbury ......... A61M 5/31535 604/207 |
| 2008/0059133 | A1 * | 3/2008 | Edwards ................ G06Q 10/00 703/7 |
| 2009/0012479 | A1 | 1/2009 | Moller et al. |
| 2009/0275914 | A1 * | 11/2009 | Harms .................... A61M 5/24 604/506 |
| 2009/0275916 | A1 | 11/2009 | Harms et al. |
| 2010/0036320 | A1 * | 2/2010 | Cox ........................ A61M 5/24 604/135 |
| 2011/0201998 | A1 * | 8/2011 | Pongpairochana ...... A61M 5/20 604/67 |
| 2012/0116311 | A1 * | 5/2012 | Bruggemann .... A61M 5/14244 604/154 |
| 2012/0265151 | A1 * | 10/2012 | Nzike ............... A61M 5/31543 604/211 |
| 2013/0046246 | A1 * | 2/2013 | Cross .................... A61M 5/326 604/189 |
| 2013/0261563 | A1 * | 10/2013 | Zachek ............... A61M 5/3213 604/263 |
| 2014/0039404 | A1 * | 2/2014 | Young ................. A61M 5/2448 604/192 |
| 2014/0039407 | A1 * | 2/2014 | Schoonmaker ..... A61M 5/3202 604/198 |
| 2015/0250954 | A1 * | 9/2015 | Keitzmann ......... A61M 5/3271 604/198 |
| 2016/0206824 | A1 * | 7/2016 | Jugl .................. A61M 5/31541 |

FOREIGN PATENT DOCUMENTS

| | | |
|---|---|---|
| EP | 0496141 A1 | 7/1992 |
| EP | 0897729 A2 | 2/1999 |
| EP | 0937471 | 8/1999 |
| EP | 0937476 | 8/1999 |
| EP | 1776975 A2 | 4/2007 |
| EP | 1974761 | 10/2008 |
| EP | 2193816 | 6/2010 |
| NO | 99/038554 | 8/1999 |
| NO | 01/010484 | 2/2001 |
| WO | 93/07922 A1 | 4/1993 |
| WO | 93/24160 A1 | 12/1993 |
| WO | 02/30495 A2 | 4/2002 |
| WO | 02/092153 A2 | 11/2002 |
| WO | 03/080160 A1 | 10/2003 |
| WO | 2006/084876 A1 | 8/2006 |
| WO | 2008/058665 A1 | 5/2008 |
| WO | 2010/066796 | 6/2010 |
| WO | 20111039217 | 4/2011 |

OTHER PUBLICATIONS

"Pen-injectors for medical use—Part 1: Pen-injectors—Requirements and test methods," International Standard, reference No. ISO 11608-1:2000(E), first edition Dec. 15, 2000, 32 pages.
International Preliminary Report on Patentability and Written Opinion in Application PCT/EP2013/068549, dated Mar. 17, 2015, 6 pages.

* cited by examiner

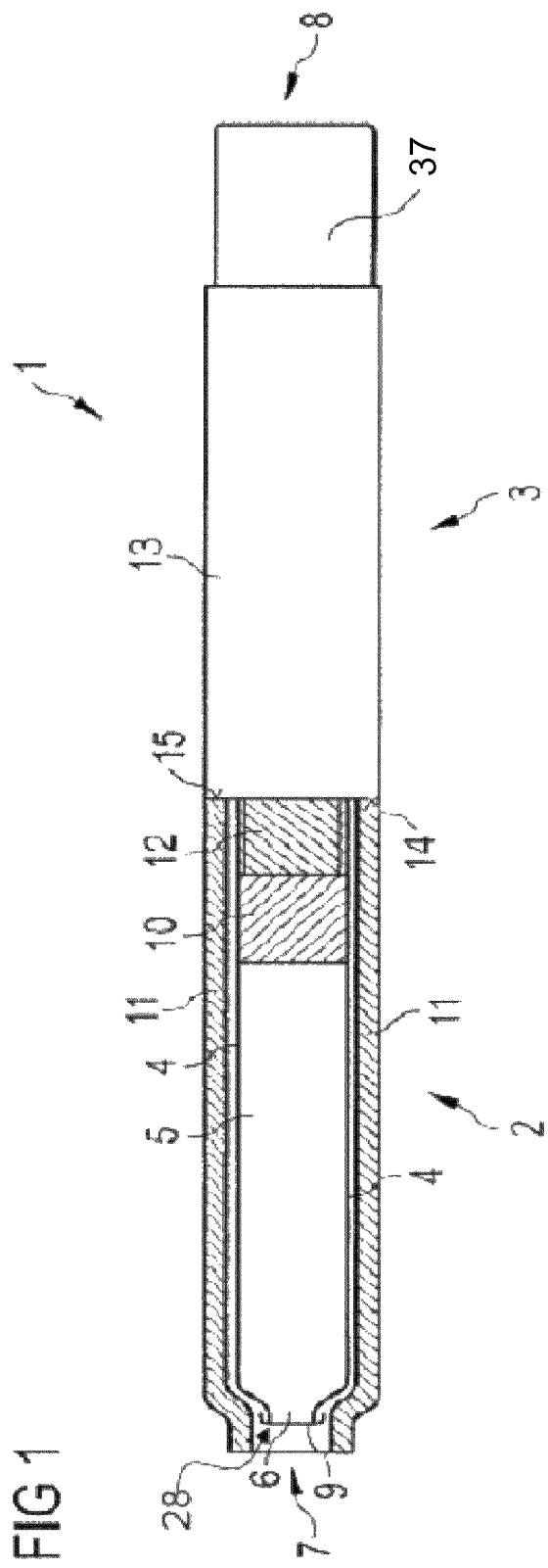

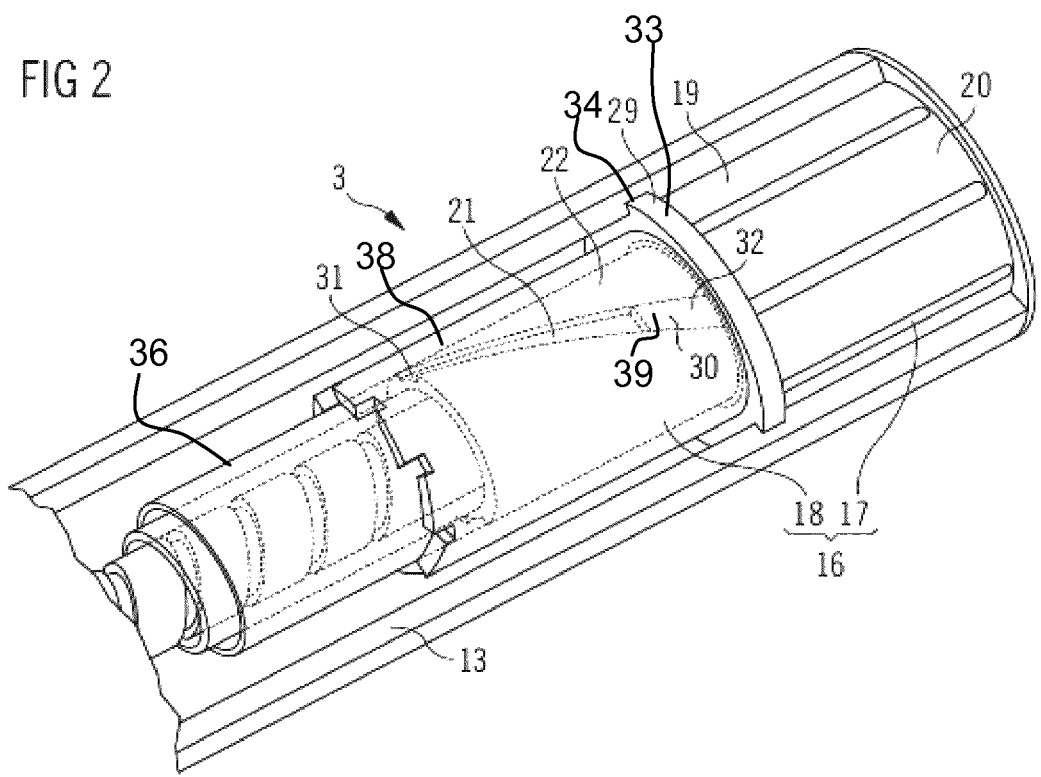
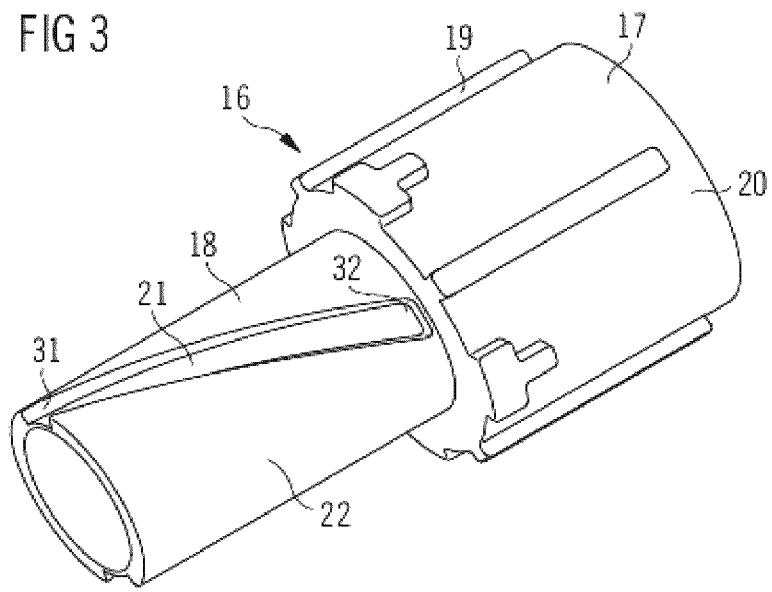

DRIVE MECHANISM FOR A DRUG DELIVERY DEVICE AND DRUG DELIVERY DEVICE

CROSS REFERENCE TO RELATED APPLICATIONS

The present application is a U.S. National Phase Application pursuant to 35 U.S.C. § 371 of International Application No. PCT/EP2013/068549 filed Sep. 9, 2013, which claims priority to European Patent Application No. 12183800.7 filed Sep. 11, 2012. The entire disclosure contents of these applications are herewith incorporated by reference into the present application.

TECHNICAL FIELD

The present invention relates to a drive mechanism for a drug delivery device and a drug delivery device incorporating such a drive mechanism.

BACKGROUND

U.S. Pat. No. 6,945,961 B2 describes a drive mechanism for a drug delivery device wherein an incremental clicking mechanism provides the user with an indication of the number of doses set. Further, US 2009/0012479 A1 discloses a drive mechanism providing non-visible feedback to a user after the end of a dose dispensing operation.

It is an object to provide for a drive mechanism providing improved user feedback. Furthermore, a novel, in particular an improved, drug delivery device is provided for.

SUMMARY

This object may be achieved by a drive mechanism according to the independent claim. Further features, advantages and expediencies are subject-matters of the dependent claims.

According to one aspect, a drive mechanism for a drug delivery device comprises a housing having a longitudinal axis, a first feedback element which is movable along the longitudinal axis relative to the housing, and a second feedback element, wherein the first feedback element and the second feedback element are adapted to interact with each other, thereby providing feedback during at least one of a dose setting and dose dispensing operation of the drive mechanism. The feedback may be non-visible. In particular, the feedback provided to a user may be at least one of an audible feedback or tactile feedback.

The term "dose setting operation" may refer to an operation that is activated by a user before a dose dispensing operation. During the dose setting operation, the drive mechanism is prepared to deliver a dose of a medication. For example, the drive mechanism may be brought into a state such that a user only needs to press a button to deliver a dose.

The term "dose dispensing operation" may refer to an operation that is activated by a user. During a dose dispensing operation, the drive mechanism may deliver a dose of a medication out of a drug delivery device.

Mechanical interaction of the first and the second feedback element may comprise, for example, interlocking, engagement, and/or abutment of the first and second feedback elements. In particular, an audible and/or tactile feedback can be provided to a user. Non-visible feedback is especially important for those users with poor eyesight.

In one embodiment, feedback may be provided to a user at least at one point during at least one of a dose setting and dose dispensing operation. Preferably, feedback is provided at least at two points during a dose setting and/or a dose dispensing operation. As an example, a double click may be provided at the beginning and at the end of a dose dispense operation. Preferably, feedback is provided at least at one point different from the beginning or the ending of the operation. Accordingly, the feedback may indicate the progress of the operation. In one embodiment, the first and second feedback element may interact with each other at least at one of a first, a second and a third point wherein the first point corresponds to 25% of the operation being completed, the second point corresponds to 50% of the operation being completed and the third point corresponds to 75% of the operation being completed. In one embodiment, the first and the second feedback element may be enabled to interact with each other continuously such that feedback may be provided continuously during at least one of a dose setting and dose dispensing operation of the drive mechanism.

The term "feedback being provided continuously" may refer to feedback that is provided during the whole time of an operation. In particular, the first and the second feedback element may be enabled to interact with each other during the whole time of a dose setting operation and/or during the whole time of a dose dispensing operation. Thereby, feedback may be provided to a user during the whole time of a dose setting operation and/or during the whole time of a dose dispensing operation.

In a preferred embodiment, the feedback is provided at least in a middle part of at least one of the dose setting operation and the dose dispensing operation. As an example, a dose setting operation and a dose dispensing operation may be divided into a beginning part, a middle part and an end part of the respective operation. The beginning part may, for example, be defined as taking up the first 20 percent of the total travel in a respective operation, the middle part may be defined as taking up the following 60 percent of the total travel and the end part may be defined as taking up the last 20 percent of the travel. As an example, feedback may be provided both at the end of at least one of the dose setting operation and the dose dispensing operation and during a middle part of the respective operation. As an example, in a preferred embodiment, feedback is provided not only during the last 20 percent of the travel of the first feedback element during at least one of a dose setting and dose dispensing operation of the drive mechanism, but also during the preceding 60 percent of the travel.

The travel of the first feedback element is defined as the axial distance by which the first feedback element moves when the drive mechanism is moved from a start position to a final position of the respective operation. In a dose setting operation, the start position of the first feedback element may be its distal end position and the final position of the first feedback element may be its proximal end position. Accordingly, in a dose dispensing operation, the start position of the first feedback element may be its proximal end position and further the final position of the first feedback element may be its distal end position. The proximal end position of the first feedback element may correspond to a state wherein a fixed dose has been set by the drive mechanism. The distal end position of the first feedback element may correspond to a state wherein the set dose has been dispensed by the drive mechanism.

According to a preferred embodiment, the drive mechanism comprises a dose member comprising the first feedback element. Preferably, the dose member is accessible to a user and is configured to be actuated by a user. The dose member can be e.g. a dose button. Said dose button can further comprise a sleeve fixed to the dose button. Preferably, the dose member is enabled to move along a longitudinal axis relative to the housing. Further, the dose member may be prevented from a rotational movement relative to the housing. In one embodiment, the dose member moves in a proximal direction relative to the housing during a dose setting operation. Further, the dose member may move in a distal direction relative to the housing during a dose delivery operation.

Preferably, the first feedback element may comprise a helical structure. Preferably, the helical structure runs helically around the longitudinal axis of the housing. A helical structure may be helpful to transform a longitudinal movement of the first feedback element into a rotational movement of another element, e.g. of the second feedback element.

According to a preferred embodiment, the first feedback element may comprise a groove. In particular, the first feedback element may comprise a helical groove. Further, the second feedback element may be guided along the groove.

Preferably, the first feedback element may comprise at least one first surface enabled to interact with the second feedback element during at least one of a dose setting and dose dispensing operation of the drive mechanism.

The first surface may interact with the second feedback element only during one of a dose setting and a dose dispensing operation. During the respective other operation of a dose setting and a dose dispensing operation, no feedback may be provided. In this case, the first feedback element may comprise a groove comprising a first and a second sidewall and a bottom and the first surface may be the surface of one sidewall of the groove. The distance between the two sidewalls may be larger than the size of the second feedback element along the direction from one sidewall to the other sidewall. Thereby, the second feedback element may interact with the first sidewall during dose setting and with the second sidewall during dose dispensing. In a preferred embodiment, feedback is provided during the dose dispensing operation and no feedback is provided during the dose setting operation.

Moreover, the first surface may interact with the second feedback element during both of a dose setting and a dose dispensing operation. In this case, the first feedback element may comprise a groove comprising a first and a second sidewall and a bottom and the first surface may be the surface of the bottom of the groove.

Said first surface may be structured. Due to an interaction of the structured first surface and the second feedback element a non-visible feedback, in particular, an audible or tactile feedback, is provided.

The surface may be structured such that the same feedback can be provided during the whole dose setting operation or respectively the whole dose dispensing operation. Alternatively, structure elements may vary on the first surface such that different feedback is provided during different phases of a dose setting or a dose dispensing operation. As an example, the feedback may be different at the beginning and at the end of the dose setting operation or, respectively, the dose dispensing operation.

In particular, the first surface may comprise structure elements, in particular protrusions or ribs. Said structure elements may be either equally spaced or spaced further apart at one end of the first surface than at another end of the first surface. If the structure elements are equally spaced apart, the same feedback can be provided during the whole dose setting operation or respectively the whole dose dispensing operation. Structure elements that are spaced further apart at one end than at the other end provide for a different feedback at the beginning and at the end of the dose setting operation or, respectively, the dose dispensing operation.

In one embodiment, structure elements may be arranged only at one end of the first surface. If the first surface interacts with the second feedback element during both a dose setting operation and a dose dispensing operation, feedback may be provided at the start of one of the operations and at the end of the other one of the operations, for example.

Moreover, the structure elements may vary in size. In particular, a bigger structure element may be provided at the beginning and/or at the end of the first surface along the longitudinal axis, thereby providing a specific feedback to indicate the beginning and/or end of a dose setting operation or a dose dispensing operation. Smaller structure elements may be provided between the beginning and the end of the first surface.

According to a preferred embodiment, the first feedback element may comprise at least one second surface enabled to interact with a second feedback element during at least one of the dose setting and dose dispensing operation of the drive mechanism. As an example, said second surface may be smooth. Due to the interaction of the second feedback element with a smooth surface, no tactile or audible feedback is provided to a user. A drive mechanism comprising a feedback element with at least one first surface and at least one second surface may be enabled to provide non-visible feedback during one of either a dose setting or dose dispensing operation. No feedback may be provided during the respective other operation.

Furthermore, the second surface may also be configured to provide feedback. This feedback could be the same feedback as the feedback being provided by an interaction of the first surface with the second feedback element. In particular, the second surface may comprise the same structure elements as the first surface, in particular protrusions, in particular ribs.

Alternatively, the second surface may comprise structure elements being different from the structure elements of the first surface regarding at least one of shape, size and quantity. Accordingly, different feedback may be provided during the dose dispensing operation and the dose setting operation.

In one embodiment, the first surface and the second surface comprise the same structure elements arranged at opposite positions. For example, the first surface may comprise structure elements at its proximal end and the second surface may comprise structure elements at its distal end. In this case, feedback may be provided at the end of a dose setting operation and at the end of a dose dispensing operation.

The first feedback element may be arranged on a sleeve. According to one embodiment, the first feedback element is arranged at the outer surface of a sleeve. Alternatively, the first feedback element may be arranged at the inner surface of a sleeve.

According to a preferred embodiment, the second feedback element may comprise a protrusion. As an example, the protrusion may be a peg. The peg interacts with the first feedback element thereby providing non-visible feedback.

Alternatively, the first feedback element may comprise a protrusion, in particular a peg. Further, the second feedback element may comprise a groove, in particular a helical groove, even more particular a helical groove comprising at least one structured surface.

According to a preferred embodiment, the second feedback element may be rotatable around the longitudinal axis of the housing. An interaction of the first and the second feedback element may transfer the axial movement of the first feedback element into a rotational movement of the second feedback element. Simultaneously, the first and the second feedback element may provide the non-visible feedback.

According to a preferred embodiment, the second feedback element may be prevented from a movement along the longitudinal axis of the housing. However, the second feedback element may be enabled to rotate around the longitudinal axis. In particular, a longitudinal movement of a drive member may be transformed into a rotational movement of the second feedback element.

The second feedback element may be an element or may be part of an element that is separated from the other elements of the drive mechanism. In particular, the drive mechanism may still be functional if the second feedback element would be removed. Alternatively, the second feedback element may be part of an element that transfers a force from one element of the drive mechanism to another element of the drive mechanism during the dose dispensing operation for causing a dispensing of a dose. In particular, the second feedback element may be part of a drive member.

Another aspect relates to a drug delivery device that comprises a drive mechanism as described above. The drug delivery device may be configured as an injection device, in particular a pen-type injection device. The device may comprise a cartridge that comprises one or more doses of a medication. The cartridge may be attached, in particular permanently or releasably attached to the housing. A piston may be arranged within the cartridge, the piston being displaceable in a distal direction with respect to the housing for delivering a dose of medication from the cartridge. A piston rod may be arranged to drive the piston in the distal direction. The drive mechanism may be configured to drive the piston rod in the distal direction. Preferably, the drive mechanism comprises a drive member which is enabled to interact directly with the piston rod.

The drive mechanism comprising a feedback mechanism as discussed keeps the user informed about an ongoing operation of the device and therefore makes the device more intuitive to use. Further, the drive mechanism enables a designer to tune the device during a design process by encoding a feeling of resistance, vibration, clicks or stops.

According to a further aspect, a member is provided comprising a first feedback element. The member may be movable along a longitudinal axis relative to a housing and the first feedback element may be enabled to interact with a second feedback element during at least one of a dose setting and dose dispensing operation of a drive mechanism. The member may be a dose member. Further, the member may comprise a groove. In particular, the groove may comprise a first end and a second end wherein the second end has a different angular orientation relative to the housing compared to the first end. In one example, the member may comprise a helical groove. The helical groove may comprise at least one structured surface.

Features which are described herein above and below in connection with the drive mechanism may also be applied for the corresponding drug delivery device and the member comprising a feedback element.

The term "medication" or "drug", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two 0 sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

Further features, refinements and expediencies become apparent from the following description of the exemplary embodiments in connection with the figures.

FIG. 1 schematically shows a partly sectional side view of an exemplary embodiment of a drug delivery device.

FIG. 2 schematically shows a perspective partly sectional view of a part of a drive mechanism according to a first embodiment.

FIG. 3 schematically shows a perspective view of a dose member.

Like elements, elements of the same kind and identically acting elements may be provided with the same reference numerals in the figures.

DETAILED DESCRIPTION

Figure 4:
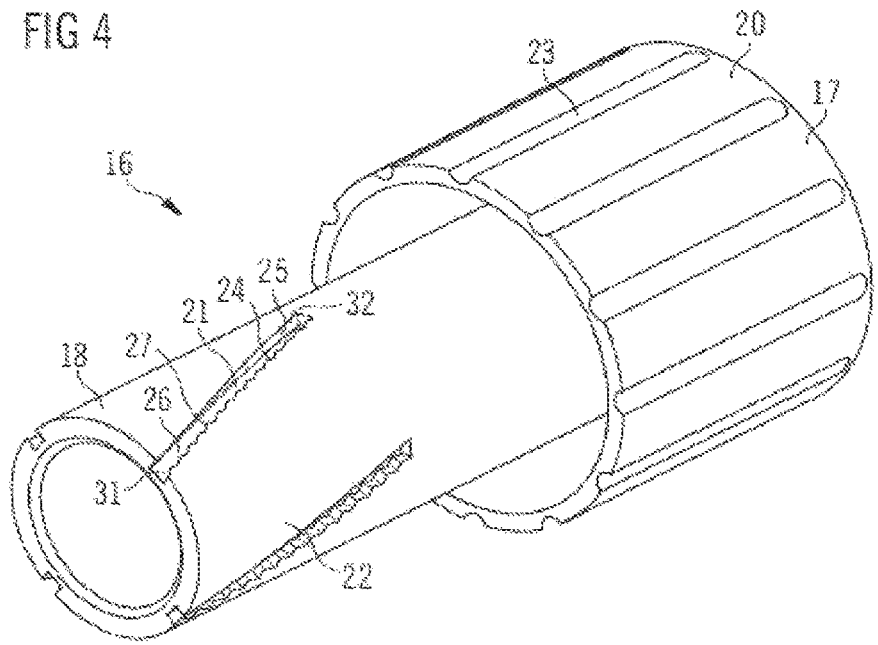
FIG. 4 schematically shows a perspective view of a dose member being part of a drive mechanism according to a first embodiment.

Turning now to FIG. 1, a drug delivery device 1 comprises a cartridge unit 2 and a drive mechanism 3. The cartridge unit 2 comprises a cartridge 4. Medication 5 is retained in the cartridge 4. The medication 5 is preferably liquid medication. The cartridge 4 preferably comprises a plurality of doses of the medication 5. The medication 5 may comprise insulin, heparin, or growth hormones, for example. The cartridge 4 has an outlet 6 at its distal end 28. Medication 5 can be dispensed from the cartridge through outlet 6. The device 1 may be a pen-type device, in particular a pen-type injector. The device 1 may be a disposable or a reusable device. The device 1 may be a device configured to dispense fixed doses of the medication or variable, preferably user-settable, doses. The device 1 may be a needle-based or a needle free device. The device 1 may be an injection device.

The term "distal end" of the medication delivery device 1 or a component thereof may refer to that end of the device or the component which is closest to the dispensing end of the device 1. The term "proximal end" of the medication delivery device 1 or a component thereof may refer to that end of the device or the component which is furthest away from the dispensing end of the device. In FIG. 1, the distal end of the device 1 is assigned reference numeral 7 and the proximal end of the device is assigned reference numeral 8.

The outlet 6 may be covered by a membrane 9, which protects medication 5 against external influences during storage of the cartridge. For medication delivery, membrane 9 may be opened, e.g. pierced. For example, membrane 9 may be pierced by a needle unit (not explicitly shown). The needle unit may be (releasably) attached to the distal end 7 of the cartridge unit 2. The needle unit may provide for fluid communication from the inside of the cartridge 4 to the outside of the cartridge through outlet 6.

A piston 10 is retained within the cartridge 4. The piston 10 is movable with respect to the cartridge 4. The piston 10 may seal the medication 5 within the cartridge 4. The piston 10 expediently seals the interior of the cartridge 4 proximally. Movement of the piston 10 with respect to the cartridge 4 in the distal direction causes medication 5 to be dispensed from the cartridge through outlet 6 during operation of the device.

The cartridge unit 2 furthermore comprises a cartridge retaining member 11. The cartridge 4 is retained within the cartridge retaining member 11. The cartridge retaining member 11 may stabilize the cartridge 4 mechanically. Additionally or alternatively, the cartridge retaining member 11 may be provided with a fixing member (not explicitly shown) for attaching the cartridge unit 2 to the drive mechanism 3.

The cartridge unit 2 and the drive mechanism 3 are secured to one another, preferably releasably secured.

The drive mechanism 3 is configured for transferring force, preferably user-exerted force, particularly preferably manually exerted force, to the piston 10 for displacing the piston 10 with respect to the cartridge 4 in the distal direction. A dose of medication 5 may be dispensed from the cartridge 4 in this way. The size of the delivered dose may be determined by the distance by which the piston 10 is displaced with respect to the cartridge 4 in the distal direction.

The drive mechanism 3 comprises a piston rod 12. The piston rod 12 may be configured for transferring force to the piston 10, thereby displacing the piston in the distal direction with respect to the cartridge 4. A distal end face of the piston rod 12 may be arranged to abut a proximal end face of the piston 10. A bearing member (not explicitly shown) may be arranged to advance the piston 10, preferably to abut the proximal end face of the piston 10.

The drive mechanism 3 comprises a housing 13. The piston rod 12 may be retained in the housing. A proximal end side 14 of the cartridge unit 2 may be secured to the drive mechanism 3 at a distal end side 15 of the housing 13, for example via a threaded connection. Housing 13, cartridge 4 and/or cartridge retaining member 11 may have a tubular shape.

The term "housing" shall preferably mean any exterior housing ("main housing", "body", "shell") or interior housing ("insert", "inner body") which may have a unidirectional axial coupling to prevent proximal movement of specific components. The housing may be designed to enable the safe, correct, and comfortable handling of the medication delivery device or any of its mechanism. Usually, it is designed to house, fix, protect, guide, and/or engage with any of the inner components of the medication delivery device (e.g., the drive mechanism, cartridge, piston, piston rod), preferably by limiting the exposure to contaminants, such as liquid, dust, dirt etc. In general, the housing may be unitary or a multipart component of tubular or non-tubular shape.

The term "piston rod" shall preferably mean a component adapted to operate through/within the housing, which may be designed to transfer axial movement through/within the drug delivery device, preferably from a drive member to the piston, for example for the purpose of discharging/dispensing an injectable product. Said piston rod may be flexible or not. It may be a simple rod, a lead-screw, a rack and pinion system, a worm gear system, or the like. "Piston rod" shall further mean a component having a circular or non-circular cross-section. It may be made of any suitable material known by a person skilled in the art and may be of unitary or multipart construction.

The drive mechanism 3 comprises a dose button 37. The dose button 37 is movable with respect to the housing 13. The dose button 37 may be movable in the proximal direction with respect to the housing for setting of a dose of the medication 5 which is to be delivered and in the distal direction with respect to the housing for delivery of the set dose. The dose button 37 is preferably connected to the housing 13. The dose button 37 may be secured against rotational movement with respect to the housing. The dose button 37 may be moved (displaced) between a proximal end position and a distal end position with respect to the housing 13 (not explicitly shown).

The device 1 may be a manually, in particular non-electrically, driven device. The (user-applied) force which causes the dose button 37 to be moved with respect to the housing 13 in the distal direction may be transferred to the piston rod 12 by a drive member. For this purpose, other elements of the drive mechanism may be provided which are not explicitly shown in FIG. 1. The drive mechanism is preferably configured to not move the piston rod 12 with respect to the housing 13 when the dose button 37 is moved in the proximal direction with respect to the housing 13 for setting of the dose.

Embodiments of a drive mechanism which are suitable to be provided in the drug delivery device 1 as it was described above are described in more detail below.

A first embodiment of a drive mechanism which is suitable for being implemented in the medication delivery device 1 as described above is described in connection with FIGS. 2 to 7.

FIG. 2 schematically shows a perspective sectional view of a part of a drive mechanism.

The drive mechanism 3 comprises a dose member 16 comprising a dose element 17 and a dose sleeve 18. The dose sleeve 18 is fixed to the dose element 17. Accordingly, the dose sleeve 18 can not move axially or rotationally relative to the dose element 17. The dose element 17 is arranged inside the housing 13. The dose element 17 may be coupled to the dose button (not shown) which may extend out of the housing 13.

The dose member 16 is movable with respect to the housing 13. The dose member 16 may be movable in the proximal direction with respect to the housing for setting a dose of the medication 5 which is to be delivered and in the distal direction with respect to the housing for delivery of the set dose. The dose member 16 is preferably engaged with the housing 13. The dose member 16 may be secured against rotational movement with respect to the housing. The dose member 16 may be moved (displaced) between a proximal end position and a distal end position with respect to the housing 13 (not explicitly shown). The distance by which the dose member 16 is displaced with respect to the housing 13 during setting of the dose may correspond to a size of the dose. The proximal end position and the distal end position may be determined by a respective stop feature which may limit the proximal or distal travel of the dose member with respect to the housing. In one embodiment, the stop feature limiting the proximal or distal travel of the dose member may be the second feedback element. In particular, the stop feature may be shaped as a ring comprising a protrusion.

To set a dose, a user may manually move dose member 16 in the proximal direction with respect to the housing 13. To do so, the user may grip the dose button and pull it in the proximal direction. Thereby, the dose element 17 and accordingly the dose member 16 move proximally also with respect to the drive member.

After the dose has been set, the dose button is moved (pushed) by the user in the distal direction with respect to housing 13. Thus, the dose member 16 is moved in the distal direction with respect to the housing 13.

The dose element 17 may comprise a guide feature, for example a guide lug or a guide slot, that engages another guide feature, for example a guide slot or a guide lug that is provided in the housing 13. The dose element 17 is preferably secured against rotational movement with respect to the housing 13. In the embodiment shown in FIG. 2, the dose element 17 comprises ribs 19 on its outer surface 20. The housing 13 comprises grooves (not explicitly shown) on its inner surface. The ribs 19 of the dose element 17 and the grooves of the housing 13 are enabled to interact with each other. The ribs 19 extend linear along a longitudinal axis of the device 1.

The ribs 19 of the dose member and the corresponding grooves of the housing 13 prevent the dose member 16 from rotational movement with respect to the housing 13. The dose member 16 is enabled to move in the proximal direction with respect to the housing 13 during dose setting. The dose member 16 is enabled to move in the distal direction with respect to the housing 13 during dose dispensing.

FIG. 3 shows a more detailed view of the dose member 16. The dose member 16 comprises a first feedback element. In particular, the dose sleeve 18 comprises a helical groove 21 on its outer surface 22 wherein the helical groove 21 is the first feedback element of the drive mechanism 3.

Further, the drive mechanism comprises an axially fixed element 29 comprising a second feedback element 30. The axially fixed element 29 may comprise a cylinder 38. Said cylinder 38 may comprise a protrusion. In particular, said cylinder 38 may comprise the second feedback element 30 which may be configured as a peg 39 that extends inwardly in the radial direction as shown in FIG. 2. The radial direction may be defined as a direction perpendicular to an axis connecting the distal end 7 and the proximal end 8 of the device.

In FIG. 2, a main part of the cylinder 38 is shown as transparent to enable the peg 39 to be visible. Furthermore, the drive mechanism may comprise a nut component 36. The nut component 36 and the cylinder 38 are in a ratcheted engagement. In particular, the cylinder 38 may be enabled to rotate in a first angular direction relative to the nut component 36. If the cylinder 38 rotates in a second angular direction, the nut component 36 is rotated relative to the housing 13 such that the cylinder 38 and the nut component 36 do not rotate relative to each other. Moreover, the nut component 36 is engaged to the piston rod 12, e.g. by a threaded or splined engagement.

The part of cylinder 38 which is visible in FIG. 2 comprises a ridge 33 extending outwardly in the radial direction. The ridge 33 may be ring-shaped. Further, the housing 13 comprises a groove 34 on its inside. The groove 34 may be ring-shaped. The ridge 33 of the cylinder 38 is engaged in the groove 34 of the housing 13 such that an axial movement of the cylinder 38 relative to the housing 13 is prevented during dose setting and dose dispensing operations.

The axially fixed element 29 comprising the second feedback element 30 has a larger diameter than the dose sleeve 18. The element 29 surrounds the outer surface 22 of the dose sleeve 18. Moreover, the axially fixed element 29 comprises the peg 39 which extends inwardly in the radial direction from the axially fixed element 29.

The second feedback element 30 is prevented from axial movement relative to the housing 13. Further, the second feedback element 30 is enabled to rotate relative to the housing 13.

The peg 39 engages with the helical groove 21 of the dose sleeve 18. The helical groove 21 comprises a first and a second sidewall 24, 25. Preferably, the width of the peg 39 is slightly smaller than the distance between the two sidewalls 24, 25. Accordingly, the peg 39 can slide along the helical groove 21, if the dose sleeve 18 is moved along the longitudinal axis. Thereby, a linear movement of the dose sleeve 18 is converted into a rotational movement of the second feedback element 30 and the axially fixed element 29.

A track of the helical groove 21 extends from a distal end 31 to a proximal end 32 of the groove 21. During a dose setting operation the peg 39 may be moved from the distal end 31 of the track to the proximal end 32 of the track. Accordingly, during a dose dispensing operation the peg 39 may be moved from the proximal end 32 of the track to the distal end 31 of the track.

Further, during dose setting, the dose member 16 may be decoupled from the piston rod 12. During dose setting, the dose member 16 is moved in the proximal direction. Accordingly, the peg 39 slides along the helical groove 21. Thereby, an axial movement of the dose member 16 is transferred into a rotation of the cylinder 38. The cylinder 38 is rotated in a first angular direction. The cylinder 38 is engaged to the nut component 36 such that rotation of the cylinder 38 in the first angular direction is not transferred to the nut component 36. Accordingly, the nut component 36 is not moved during dose setting.

However, during dose dispensing, the dose member 16 interacts with the piston rod 12. The dose member 16 can either engage directly with the piston rod 12 or the dose member 16 may engage with a drive member, e.g. a drive sleeve, engaging with the piston rod 12. Thereby, a movement of the dose member 16 in the distal direction is transferred into a movement of the drive member. The drive member may also move linearly in the distal direction or the drive member may carry out a rotational movement around the longitudinal axis of the housing 13.

Furthermore, during a dose dispense operation of the dose member 16, a distal movement of the dose member 16 is transferred into a movement of the piston rod 12. In particular, a distal movement of the dose member 16 may be transferred into a rotational movement of cylinder 38 relative to the housing 13 as the peg 30 slides along the helical groove 21. The cylinder 38 is rotated anti-clockwise. The cylinder 38 is engaged to the nut component 36, e.g. by a ratchet connection, such that a rotation of the cylinder 38 in a second angular direction is transferred into a rotation of the nut component 36.

The piston rod 12 may be either splined or threadedly engaged to the nut component 36. Further, the piston rod 12 has a threaded or splined connection to the housing 13. If the piston rod 12 is threadedly engaged to the nut component 36 and the piston rod 12 is splined to the housing 13, a rotation of the nut component 36 does not rotate the piston rod 12, but advances the piston rod 12 distally. If the piston rod 12 is splined to the nut component 36 and threaded to the housing 13, then the piston rod 12 will be rotated and advance distally if the nut component 36 rotates.

When the piston rod 12 is moved into the distal direction, the piston rod 12 pushes the piston 10 into the cartridge 4 in the distal direction.

The distance by which the piston rod 12 is moved corresponds to the delivered dose. This distance is defined by the amount of rotation of the nut component 36. The amount of rotation of the nut component 36 is determined by the relative angular positions of the the proximal end 32 and distal end 31 of the track of the helical groove corresponding to the start and finish positions of the peg 30 in the groove 21.

FIG. 3 shows a dose member 16 comprising a dose element 17 and a dose sleeve 18 wherein the dose sleeve 18 is fixed to the dose element 17. The dose element 17 comprises ribs 19 on its outer surface 20 thereby enabling an axial movement of the dose member 16 relative to the housing 13 and preventing a rotational movement of the dose member 16 relative to the housing 13. The dose sleeve 18 comprises helical grooves 21 on its outer surface 22 thereby enabling an interaction of the dose member 16 with the second feedback element wherein an axial movement of the dose member 16 relative to the housing 13 is converted into a rotational movement of the second feedback element relative to the housing 13. The helical groove 21 comprises a first and a second sidewall 24, 25 and a bottom 26. At least one of a first and a second sidewall 24, 25 and a bottom 26 may comprise a structured surface.

In an alternative embodiment, the second feedback 30 element may be part of a member positioned inside the dose sleeve 18. As an example, the second feedback 30 may be provided by a drive member, in particular it may be part of a drive sleeve. In this case, the second feedback element 30 may be positioned inside the dose sleeve 18. The first feedback element may be provided on another member positioned inside the dose sleeve 18 or on the inner surface of the dose sleeve 18.

In particular, the feedback mechanism could be a mechanism separate from the drive mechanism. In particular, the first and second feedback elements could be provided by member separate from the drive member and the dose member. In the case that the feedback mechanism is separate from the drive mechanism, the feedback performance could be made independent of the drive force. As an example, the first and second feedback elements could be pressed together with a controlled force provided by a spring.

However, if the feedback mechanism is integrated into the drive mechanism, fewer parts may be necessary to construct the device.

Figure 5:
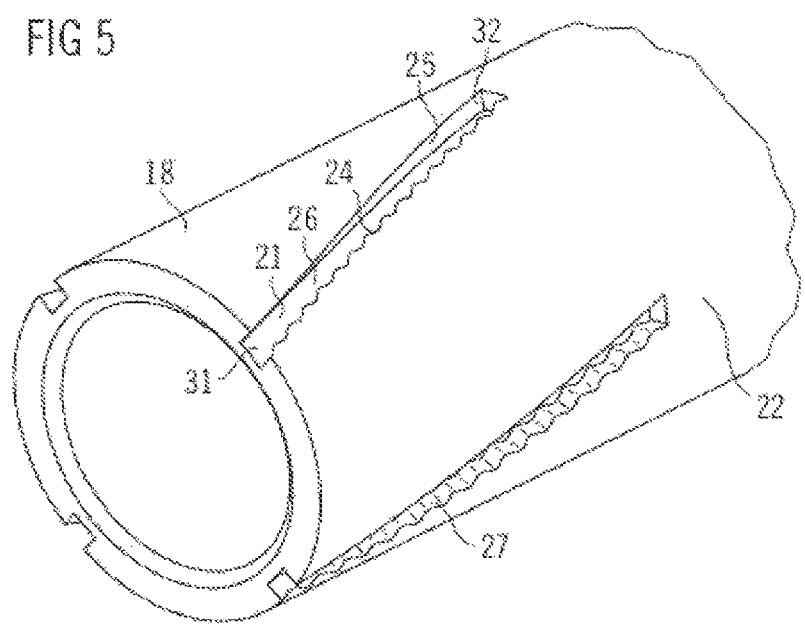
FIG. 5 shows a more detailed perspective view of a part of FIG. 4.

FIGS. 4 and 5 show a dose member 16 comprising a first feedback element according to a first embodiment. The dose member 16 comprises a dose element 17 and a dose sleeve 18. The dose element 17 comprises slots 23 on its outer surface 22. A user interacts directly with the outer surface 22. The slots 23 simplify the gripping of the dose element 17.

The dose sleeve 18 comprises a helical groove 21 which comprises a first sidewall 24 with a first surface, a second sidewall 25 with a second surface and a bottom 26 with a third surface. The first surface of the first sidewall 24 is structured and the second surface of the second sidewall 25 is smooth. During dose setting, the dose member 16 moves in the proximal direction relative to the housing 13. Accordingly, during dose setting, the dose sleeve 18 moves in the proximal direction relative to the second feedback element 30 and the axially fixed element 29. Accordingly, the peg 39 will run on the second surface of the second sidewall 25 of the helical groove 21. As the second surface is smooth, no audible or tactile feedback is provided thereby.

During dose dispensing, the peg 39 will run on the first surface of the first sidewall 24 as the dose sleeve 18 moves in the distal direction relative to the peg 39. The first surface of the first sidewall 24 comprises a structure. In the embodiment shown in FIGS. 4 and 5, the first surface of the first sidewall 24 comprises ribs 27.

During a dose dispensing operation, the peg will contact the first surface of the first sidewall 24 comprising ribs 27, thereby causing a tactile sensation to be transmitted to a user. Accordingly, the interaction of the ribbed surface of the first sidewall 24 and the peg 39 provides tactile feedback to the user. Moreover, the interaction of the peg 39 and the ribbed surface of the first sidewall 24 of the helical groove 21 may also provide audible feedback.

Accordingly, a dose member 16 according to the first embodiment provides non-visible feedback to a user only during a dose dispensing operation. During dose setting, no feedback is provided to the user.

Alternatively, the surfaces of the sidewalls 24, 25 of the helical groove 21 may be chosen in a way that, during dose setting, the peg interacts with a structured surface and, during dose dispensing, the peg interacts with a smooth surface. Thereby, non-visible feedback is provided to a user during dose setting. No non-visible feedback is provided to a user during dose dispensing.

Figure 8:
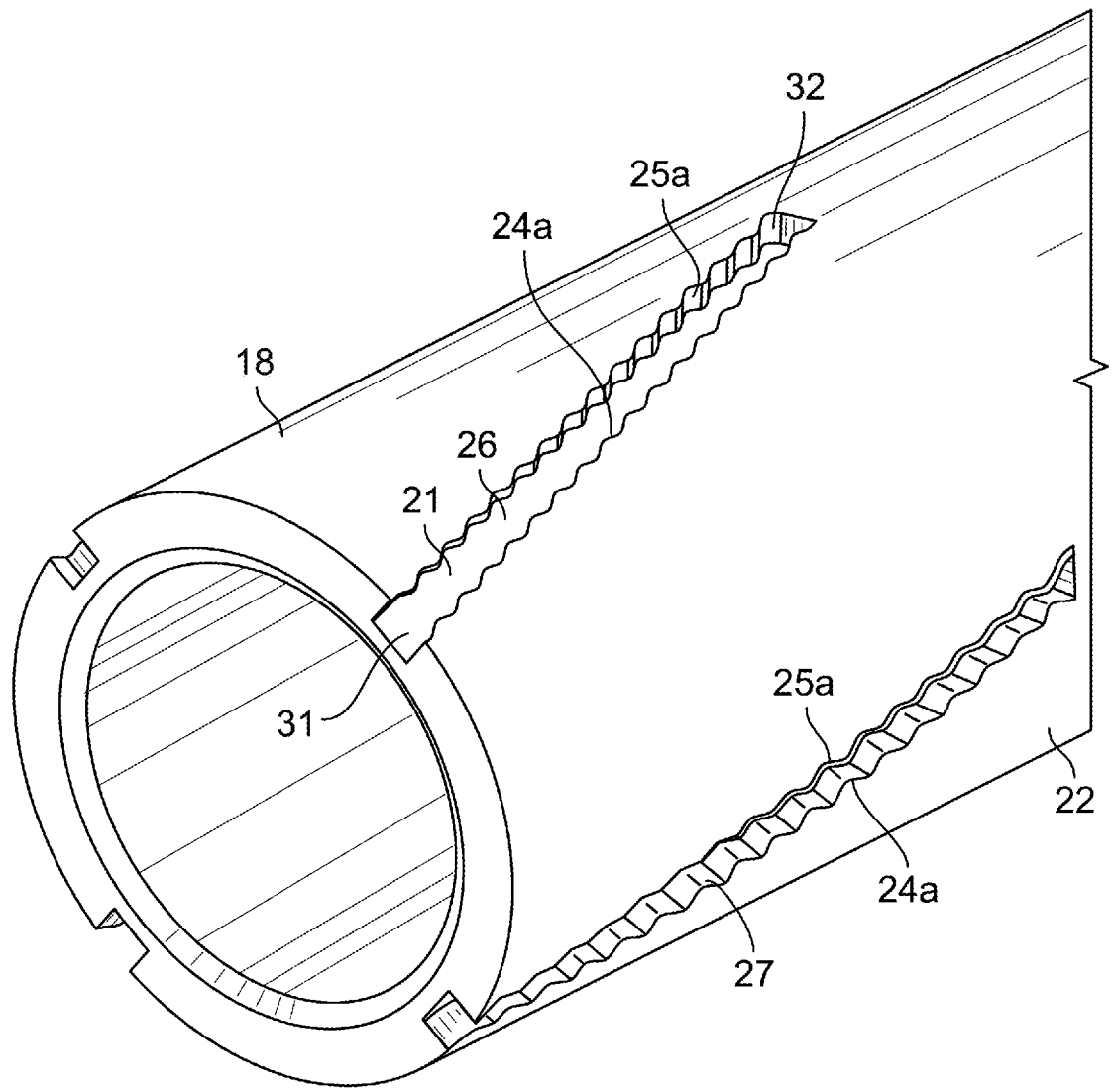
FIG. 8 illustrates a more detailed perspective view of a part of FIG. 4 with alternative helical grooves where both side walls have structured surfaces.

In a further embodiment, sidewalls 24 and 25 each comprise a structured surface 24a and 25b, respectively (see FIG. 8). Thereby non-visible feedback can be provided to a user during both dose setting and dose dispensing.

In the embodiment of the dose member 16 as shown in FIGS. 4 and 5, the ribs 27 are equally spaced apart from each other. Accordingly, during the whole time of a dose dispensing operation, the same feedback is provided to the user.

It is also possible to configure the first feedback element such that ribs 27 differ in size and/or spacing along a track of the helical groove 21. For example, the ribs 27 can be spaced further apart from each other at the proximal end 32 of the track of the helical groove 21 than at the distal end 31 of the track of the helical groove 21. Accordingly, at the beginning of the dose dispensing operation, the peg interacts with ribs 27 that are spaced further apart. Towards the end of the dose dispensing operation, the peg interacts with ribs 27 that are spaced closer together. This may give the illusion to the user that the dose member 16 is accelerating when the user pushes the dose member 16 in. Therefore, the users will slow the dispensing stroke down as the peg approaches the end of the track of the groove 21. Thereby the user may be prevented from overstraining the device 1.

Figure 6:
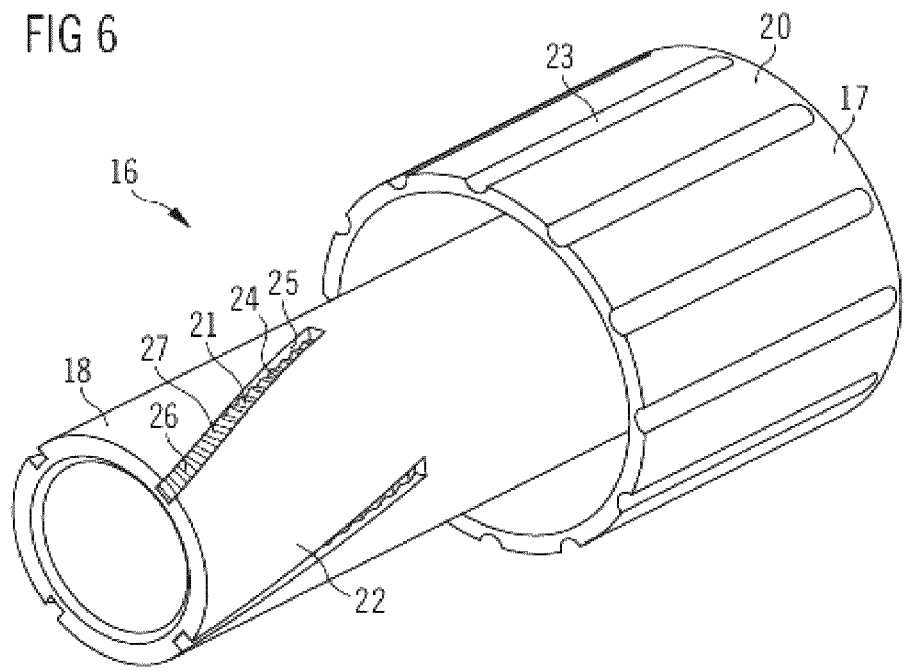
FIG. 6 schematically shows a perspective view of a drive mechanism according to a second embodiment.
Figure 7:
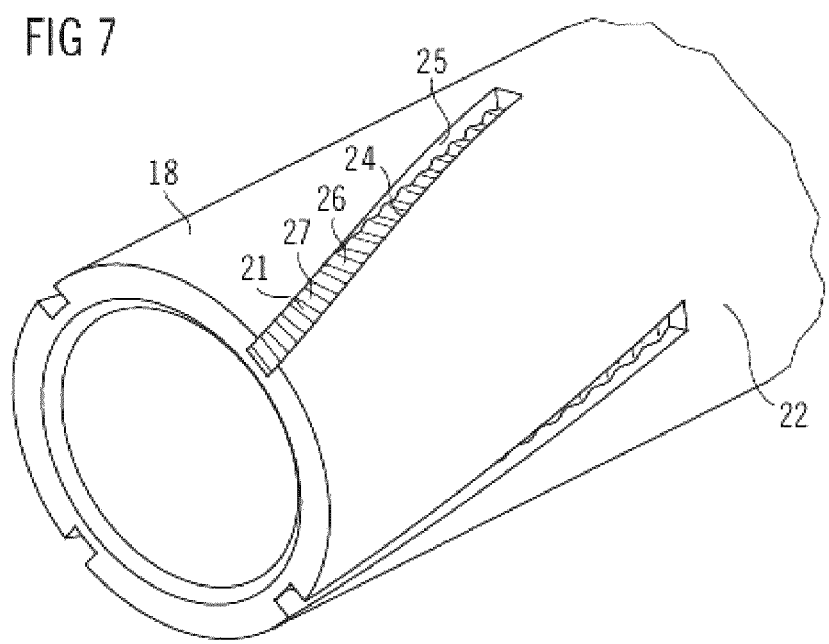
FIG. 7 schematically shows a perspective view of a part of FIG. 6.

FIGS. 6 and 7 show a dose member 16 comprising a first feedback element according to a second embodiment. The dose member 16 differs from the dose member 16 shown in FIGS. 4 and 5 in that, here, the surfaces of the sidewalls 24, 25 of a helical groove 21 are smooth. Further, the surface of the bottom 26 of the helical groove 21 is ribbed. The mating peg interacts with the bottom 26 of the helical groove 21 during both dose setting and dose dispensing. Accordingly, during both operations, the peg is enabled to interact with a structured surface. Therefore, non-visible feedback is provided to a user during dose setting and during dose dispensing.

Further variations of the feedback mechanism are possible. Additionally to a structured surface, a single rib to signal the end of the dose setting or dose dispensing operation could be provided at one end of the helical groove 21 on at least one of its surfaces. Further, a double rib to indicate that a complete dose has been set or dispensed could be provided at one end of the helical groove 21. This would alert the user through either a feeling and/or a sound that the limits of travel have been reached without the need for them to overstrain the device 1. The single rib and/or the double ribs may be provided either on a surface being smooth apart from said ribs or on a surface comprising further structure elements.

The invention claimed is:

1. A drive mechanism for a drug delivery device, comprising:
    a housing having a longitudinal axis,
    a first feedback element which is movable along the longitudinal axis relative to the housing, the first feedback element comprising a helical structure, and
    a second feedback element,
    wherein the first feedback element and the second feedback element are adapted to interact with each other, thereby providing at least one of tactile and audible feedback during a dose setting operation of the drive mechanism,
    wherein the first feedback element comprises a first surface configured to interact with the second feedback element during a dose setting operation of the drive mechanism, wherein the first surface comprises first protrusions, the first feedback element comprises a second surface comprising second protrusions, wherein the first and second protrusions are arranged opposite one another to result in an audible or tactile feedback when interacting with the second feedback element, and wherein the second protrusions are configured to interact with the second feedback element during at least one of the dose setting and a dose dispensing operation of the drive mechanism.

2. The drive mechanism according to claim 1, wherein the first feedback element and the second feedback element are configured to provide feedback during at least one of a dose setting and dose dispensing operation of the drive mechanism.

3. The drive mechanism according to claim 1, comprising a dose member which comprises the first feedback element.

4. The drive mechanism according to claim 1, wherein the first surface comprises the first protrusions at its proximal end and the second surface comprises the second protrusions at its distal end.

5. The drive mechanism according to claim 1, wherein the first feedback element comprises a groove.

6. The drive mechanism according to claim 1, wherein the first protrusions are equally spaced along the first surface.

7. The drive mechanism according to claim 1, wherein the first protrusions are spaced further apart at one end of the first surface than at another end of the first surface.

8. The drive mechanism according to claim 1, wherein the second surface is configured to interact with the second feedback element during at least one of a dose setting and dose dispensing operation of the drive mechanism.

9. The drive mechanism according to claim 1, comprising a sleeve, wherein the first feedback element is arranged at a surface of the sleeve.

10. The drive mechanism according to claim 1, wherein the second feedback element comprises a peg.

11. The drive mechanism according to claim 1, wherein the second feedback element is rotatable around the longitudinal axis of the housing.

12. The drive mechanism according to claim 1, wherein the second feedback element is prevented from moving along the longitudinal axis of the housing.

13. A drug delivery device comprising the drive mechanism according to claim 1.

* * * * *